United States Patent [19]

Halpaap et al.

[11] 4,158,626

[45] Jun. 19, 1979

[54] COATED CARRIER MATERIALS FOR THIN LAYER CHROMATOGRAPHY HAVING A CONCENTRATING ZONE

[75] Inventors: Herbert Halpaap, Jugenheim; Karl-Friedrich Krebs, Darmstadt; Hans Heinz, Lorsch, all of Fed. Rep. of Germany

[73] Assignee: Merck Patent Gesellschaft mit beschränkter Haftung, Darmstadt, Fed. Rep. of Germany

[21] Appl. No.: 909,591

[22] Filed: May 25, 1978

[30] Foreign Application Priority Data

May 31, 1977 [DE] Fed. Rep. of Germany ....... 2724569

[51] Int. Cl.$^2$ ............................................. B01D 15/08

[52] U.S. Cl. ................................. 210/31 C; 210/198 C
[58] Field of Search .......................... 210/31 C, 198 C

[56] References Cited

U.S. PATENT DOCUMENTS 3,303,043   2/1967   Halpaap et al. ................. 210/198 C Primary Examiner—John Adee
Attorney, Agent, or Firm—Millen & White

[57] ABSTRACT

TLC plates having a concentrating zone located adjacent to and before a chromatography layer are improved by using as the layer for the concentrating zone a silicon dioxide of medium pore volume (e.g., 0.5–1.5 ml/g) and a pore width of 2–15 μm.

10 Claims, No Drawings

4,158,626

COATED CARRIER MATERIALS FOR THIN LAYER CHROMATOGRAPHY HAVING A CONCENTRATING ZONE

BACKGROUND OF THE INVENTION

The present invention relates to an improvement in thin layer chromatography plates containing concentrating zones.

A series of carrier materials are commercially available, preferably glass plates or also synthetic resin or aluminum foil plates, which are coated with layers suitable for chromatography, especially for thin layer chromatography (TLC), e.g., layers of silica gel. It is also already known to provide a low or non-adsorptive layer of kieselguhr adjacent to and forward of the chromatographically active silica gel layers. Such a layer is termed a concentrating zone.

Because of the differing adsorption properties of the two sorption agents, such as kieselguhr and silica gel, on 200 μcommon substrate, it is possible to exactly evaluate chromatograms even when samples are not uniformly applied.

In such known concentrating zone-containing TLC plates, the test sample is applied in the concentrating zone. When the eluent is thereafter applied, the entire sample moves rapidly through the practically inactive layer of the concentrating zone up to its very narrow border with the chromatographic zone. At this junction region, all components of the test sample are greatly retarded due to the adsorptive properties of the chromatography layer such as silica gel resulting in a collision-like deacceleration of all components in the test sample. As a result, irrespective of the broadness of the original pattern of the test sample as applied in the concentrating zone, the pattern becomes sharply defined when it enters the chromatography zone.

Whereas for the chromatography layer, the proven silica gel layers are preferably used, hitherto kieselguhr has been used for the inactive concentrating zone. Because of its activity, normal silica gel is not suitable for this purpose. However, the known TLC preparations having such a kieselguhr layer possess considerable deficiencies which result from the properties of the kieselguhr. As a natural product, the quality and properties of the kieselguhr are dependent upon the source from which it is obtained. In addition, very laborious methods of purification are required in order to obtain a material useful for this purpose. Coloring components present in the kieselguhr must be removed; however, very frequently it is not possible to eliminate inorganic salts or traces of heavy metals remaining in the kieselguhr, which disturb the chromatography.

SUMMARY OF THE INVENTION

Accordingly, it is an object of the present invention to provide improved chromatographic plates with a concentrating zone which, especially do not have the disadvantages attendant to the use of kieselguhr therein.

Upon further study of the specification and appended claims, further objects and advantages of this invention will become apparent to those skilled in the art.

These objects have been attained by providing especially advantageous coated carrier materials for layer chromatography having a concentrating zone before the chromatographic zone wherein the concentrating zone layer consists essentially of a synthetically produced, porous silicon dioxide of medium pore volume and very high pore width (pore diameter). As a result, an extremely good spreading out of the applied sample in the concentrating zone is achieved. This acts very favorably on the following chromatography.

This invention moreover relates to coated carrier materials for thin layer chromatography having a concentrating zone layer placed before the chromatography layer, which are improved in that the concentrating zone consists essentially of a synthetically produced, porous silicon dioxide layer having medium pore volume and a pore width of 2 to 15 μm.

Especially advantageously, the silicon dioxide of the concentrating zone should have particle sizes in the range of 10 to 50 μm. Furthermore, it is especially advantageous that the layer thickness of the concentrating zone be about 100 to 200, preferably about 150 μm.

Furthermore, this invention relates to a method of separating components in a test sample and of highly concentrating all components of a test sample as it enters a chromatography layer which comprises placing the sample in a concentrating zone located before the adjacent to the chromatography layer, the concentrating zone consisting essentially of a synthetically produced, chromatographically inactive, porous silicon dioxide of medium pore volume and a pore width of 2 to 15, preferably 4 to 8 μm; and subsequently placing eluent into the concentrating zone so that the test sample flows from the concentrating zone into the chromatography layer.

DETAILED DISCUSSION

The silicon dioxide to be used for the concentrating zone is produced in known manner by pore widening. Such methods are described in the literature, for example in U.S. Pat. Nos. 1,665,264; 3,203,760; 3,417,028; and 3,493,341. Any commercially available, synthetically produced silica gels suitable for chromatographic purpose can be employed as starting materials, preferably types having a medium pore volume. In particular, both narrow and medium width pore types can be used. A very frequently used silica gel (silica gel 60) has e.g., a pore width of about 5 to 7 nm. The particle size of the starting material can be chosen as desired but, in general, corresponds approximately to the particle size of the silica gel used, for the chromatographic layer.

The pore widening necessary for meeting the requirements of the $SiO_2$ needed for use in this invention is effected in known manner, e.g., by impregnation of the starting material silica gels with a salt solution, for example an aqueous sodium chloride or sodium sulfate solution, and subsequent calcination. After being washed out, the wide-pore silicon dioxide obtained is classified in conventional fashion. Wide-pored silica gels suitable for use as the concentrating zone layer should be narrowly classified to have an average pore volume and an extremely high pore width, as well as an extremely low specific surface area connected therewith as detailed herein.

Especially well suited are silicon dioxides having the following properties:

(a) PORE WIDTH

The pore width should be 2–15 μm, preferably 2–8 μm. The pore widths are preferably above 4 μm, e.g., 4–8 μm. The pore widths are conventionally determined, preferably using a mercury porosimeter.

(b) SPECIFIC SURFACE AREA

This property is determined using the known BET method. The specific surface area of the silicon dioxides to be used according to this invention should be <1 m$^2$/g, preferably 0.2–0.8 m$^2$/g.

(c) PORE VOLUME

The pore volume is determined using a mercury porosimeter. The silicon dioxide to be used in this invention should possess a pore volume of 0.5 ml/g–1.5 ml/g, preferably 0.5–1.0 ml/g. Such values are referred to herein as average pore volumes.

(d) PARTICLE SIZE

The particle size of the silicon dioxide should be in the range of 10–50 μm, preferably 10–20 μm. The particle size distribution within this range is not critical.

These synthetically produced silicon dioxides exhibit a very high degree of purity. A typical analysis for the maximum content of impurities, e.g., is as follows:

| | | |
|---|---|---|
| chloride (Cl): | 0.008% | |
| sulphate (SO$_4$): | 0.003% | |
| nitrate (NO$_3$): | 0.005% | |
| lead (Pb): | 0.0005% | |
| copper (Cu): | 0.0005% | |
| iron (Fe): | 0.002% | |
| zinc (Zn): | 0.0005% | |

The suitability of a given wide-pored silicon dioxide for use according to this invention can also be ascertained, e.g., by the following test:

TLC plates or foils having concentrating zones are produced according to the methods described in the Examples. 10μl of a solution of the dyestuffs, Ceres violet BRN pure, Ceres green BB and Blue 18.90 Sandoz, each of a concentration of 0.01% (w/v) in toluene, are applied to the concentrating zone lying horizontally, using a calibrated micrometer syringe combination within a period of 10 sec., whereby the solution spreads out in the form of a circle. After the expiration of an additional 10 sec., the solvent is evaporated off using a current of cold air. A circular area will have formed, the outermost narrow edge of which is of increased intensity. If the circular area has a diameter of at least 16 mm, the silicon dioxide layer is suitable for use in this invention.

The techniques of employing the silicon dioxides of this invention to produce the concentrating zones of TLC plates or foils are fully conventional.

Suitable carriers include all conventional materials, glass plates being preferred. However, it is also conventional to use foils, e.g., aluminum or synthetic resin foils. As usual, the sorption agents are slurried in coatable, mostly aqueous, suspensions. After intensive mixing and optional degassing, they are applied to the carrier materials using conventional spreading apparatus or coating devices. For the chromatography layer, there can be employed all otherwise conventionally used sorption agents, e.g., silica gels (with various pore widths between 4 and 1000 nm), aluminum oxides, celluloses, magnesium silicates and polyamides. The silica gels can also have modified (e.g., silanized) surfaces. Binding agents are usually added to the sorption agents to increase the adhesion and resistance to rubbing off. Indicators are also usually included. As binding agents, there are preferred the binding agents mentioned in German Pat. No. 1,442,446 or in accepted German patent application No. 1,517,929. The most frequently used indicator is a fluorescent indicator, preferably the manganese-activated zinc silicate absorbing at 254 nm in the UV. As a rule, the binding agents are added in amounts of 0.1–10 wt.% and the indicators in amounts of about 0.5–5 wt.%, in each case referred to the composition of the finished layer, i.e., ready for chromatographic use.

The spreading apparatus or coating plant are so arranged that the sorption agent layers provided for the chromatography border directly on the narrower layer of the concentrating zone and the two layers are in adjoining contact, their boundary defining a straight line. In the case of a coating of, e.g., glass plates of the usual format of 20×20 cm., the chromatography layer typically has a length of about 175 mm, and the concentrating zone a length of about 25 mm. Generally, the ratio of the length of the concentrating zone to that of the chromatography zone is 0.2–0.1. Typical plate widths are 10–20 cm., and plate lengths are about 20 cm.

Very frequently, the layer thickness of the two zones is varied. Thus, e.g., in a preferred embodiment, the actual chromatography layer is about 250 μm thick, whereas the layer thickness of the concentrating zone is about 150 μm. Generally, the thickness of the chromatography layer is 200–300 μm, and of the concentrating zone 100–200 μm.

After the coating operation, the layered plates are dried in the usual way. As a rule, the coating conditions are so adjusted that, after drying, the layer thicknesses lie between 100 and 300 μm. The drying usually takes place in drying channels at temperatures of about 120° to 150° C. The drying period depends upon the length of the drying channel.

Chromatography plates containing the silicon dioxide concentrating zones of this invention possess surprising advantages. Compared with the conventional TLC preparations having combination layers, they exhibit a markedly better separation capacity for chromatography layers of equal quality. It could not have been foreseen that these advantages would be achieved using the silicon dioxides of this invention. Therefore, hitherto, the skilled artisan has continually used other materials, especially kieselguhr, although their disadvantages were well known.

A special advantage of the new materials also consists in the fact that very good throughput rates can be achieved. Although the two layers sharply bound one another, they, nevertheless, merge such that the elution agent experiences no resistance when passing through the boundary. Also, the correlation of the layers with regard to additive contents, such as binding agents and indicators, which is now possible for the first time, is a considerable advantage.

During actual use, the new materials having concentrating zones per this invention possess considerable advantages. After punctate or circular-shaped application of the samples, during the development procedure period while the sample is in the concentrating zone, it is automatically concentrated to a narrow start line from which the actual chromatography starts without interruption, irrespective of the Rf value of the compounds to be chromatographed.

Apart from this concentration effect, a purification also occurs directly on the plate in the concentrating zone. Advantages can be taken of this effect to eliminate the extraction of the active materials to be chromatographed which, otherwise, under certain circumstances is necessary. Inorganic and organic salts are bound in the concentrating zone, and in part also polar neutral materials, such as, for example, sugars.

The application can be carried out without special care with regard to geometry and extent of the applied spot. Consequently, the plates or foils having concentrating zones per this invention provide a considerable savings of time. Furthermore, decomposition or irreversible adsorption of sensitive substances in the test sample by the highly active silica gel, which normally occurs when the spot dries after conventional application to the chromatography zone, is avoided. The contact of such substances with the actual sorption agent takes place only after passing through the concentrating zone where it is in the dissolved state. In this sense, there occurs in effect a wet dosing as in HPLC.

It is also possible to apply samples by dipping rather than by application in lines with an application device. A better application in lines cannot be achieved even with an automatic application device. When using a highly dilute solution, with appropriate intermediate drying, the solution is applied in lines several times in order to apply the required amount of substance to the chromatographic development. The application by dipping per this invention also permits starting from very dilute solutions. In the past, for this method of application by dipping with conventional silica gel finished plates without a concentrating zone, concentration of the sample to a single band could only be achieved by developing several times with a strongly polar elution agent on a new front over the level of immersion before starting with the actual chromatography. In contradistinction, the TLC preparations having a concentrating zone per this invention offer the advantage of continuous operation with such samples and others, of course. Furthermore, ballast materials, such as inorganic or organic salts or certain polar neutral materials are held back in the concentrating zone. Due to the more favorable starting positions at the beginning of the actual chromatography, the separation capacities are also significantly improved. This is especially noticeable for comparatively large applied amounts, but also for very dilute solutions. The new materials are especially suitable for separation problems in which differing amounts of materials of interest, e.g., active ingredients, and other accompanying materials are present; so that separations in biochemistry, in clinical chemistry and in pharmaceutical quality control proceed especially successfully.

The new coated separation materials can be used everywhere that conventional TLC plates and foils are used and in the same manner.

Moreover, all aspects of the TLC plates of this invention not otherwise discussed herein are fully conventional including, inter alia, suitable conventional sorption agents, dimensions of square or rectangular plates, techniques of preparation and use of the plates, choice of sample application method, solvents, development techniques and reagents, visualization methods, etc. Details of such aspects are fully conventional and are disclosed, for example, in *Thin Layer Chromatography*, J. M. Bobbitt, Reinhold Publishing Company (N.Y. 1963), whose disclosures are incorporated by reference herein.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

EXAMPLE 1

(a) 800 g of sodium polyacrylate are added, with stirring, to 88 l of desalinated water. 38.4 kg of a medium pore size silica gel (medium pore width—6 nm) having an average particle size of 15 μm, as well as 800 g of a zinc silicate activated with manganese, are then stirred in. The suspension is adjusted with aqueous sodium hydroxide solution to a pH value of about 6.5. While stirring, make-up water is added to achieve a final total weight of 136 kg.

(b) 60 g of sodium polyacrylate are added, with stirring, to 7.8 l of desalinated water. Then, while stirring, there are introduced 60 g of a zinc silicate activated with manganese, as well as 2.88 kg of a porous silicon dioxide with the following characteristics:

| average particle size | 15 to 20μm |
|---|---|
| average pore width | 4 to 15μm |
| pore volume | 0.5 to 1.0 ml/g |
| specific surface area | 0.4 to 0.8 m$^2$/g |

(c) The two suspensions obtained according to (a) and (b) are degassed. They are placed into a coating plant for coating glass plates of the format 20×20 cm in such a manner that a layer of 175 mm breadth resulting from the suspension (a) bounds directly onto a layer of 25 mm breadth obtained from the suspension (b). The coating plant is so adjusted that, the suspension (b). The coating plant is so adjusted that, after drying, there result layer thicknesses of about 250 μm for the chromatography layer and of about 150 μm for the concentrating zone. The drying of the plates takes place in a drying channel for about 10 minutes at 150° C.

EXAMPLE 2

The suspensions (a) and (b) are prepared analogously to Example 1.

200 mm wide rolls of an aluminum band or of a synthetic resin foil (terephthalate foil of 0.2 mm thickness) are coated on the coating plant with the degassed suspensions. A chromatography layer of 175 mm breadth bounds directly onto a concentrating zone of 25 mm breadth.

EXAMPLE 3

(a) A suspension is prepared analogously to Example 1 (a) with the use of 39.2 kg of a medium pore size silica gel (pore width 5 to 7 nm) having an average particle size of 5 to 10 μm.

(b) A suspension is prepared analogously to Example I (b) with the use of 2.94 kg of a wide-pore silicon dioxide having

| average particle size | 15 to 20μm |
|---|---|
| average pore width | about 8μm |
| pore volume | about 0.8 ml/g |
| specific surface area | about 0.7 m$^2$/g |

(c) The further working up and coating takes place analogously to Example 1 (c).

On the plates obtained, the chromatography layer of 175 mm breadth borders directly onto the concentrating zone of 25 mm breadth. The plates are subsequently cut in half to give plates of the format 10×20 cm.

EXAMPLE 4

(a) 1000 g of a commercially available, microcrystalline cellulose for thin layer chromatography, 3.45 l of desalinated water and 50 ml of a 1% aqueous solution of the sodium salt of carboxymethylcellulose are intensively mixed.

(b) 4 g of sodium polymethacrylic acid are added, with stirring, to 520 ml of desalinated water. 196 g of the silicon dioxide described in Example 3 (b) are then stirred in. While stirring, the suspension is adjusted to a pH value of 6.5 with aqueous sodium hydroxide solution.

(c) The coating takes place analogously to Example 1 (c). The cellulose layer provided for the chromatography bounds directly onto a concentrating zone of 25 mm width.

EXAMPLES OF USE

EXAMPLE A

Onto the plates obtained according to Example 1, there are applied 6 random areas of a 0.1% solution of a mixture of lipophilic dyestuffs. It does not matter at which height on the concentrating zone the application takes place. In every case, after the concentration to a narrow line, the separated substances appear in the chromatography layer with identical Rf values.

Different application amounts are applied, namely, 2, 4, 8, 12, 16 and 20μl (each value also corresponding to the number of μg), in punctate form about 12 mm from the lower edge. The development takes place in a standard chamber, without chamber saturation, using toluene, up to a running height of 10 cm in the silica gel layer (=running stretch from the boundary line up to the elution agent front).

The samples applied in comparatively large amounts to the concentrating zone assume a quite large circular area. The uniform coloration of the inner circular area depends upon the practically ideal inert property of this layer. Depending upon the circle diameter, the substance mixture is concentrated on the boundary line to a narrow line of length about the same as the diameter. The tail formation after a single development up to the boundary line, which is very clear when large amounts are applied and scarcely visible for application of comparatively small amounts, is, for comparatively large elution agent flowthrough, completely removed during the actual chromatography. All substances display identical Rf values irrespective of the amount applied. Of course, with increasing applied amounts, the resolution between neighboring pairs of substances decreases somewhat, but, even in the case of applied spots of 20μg of substance, the resolution is still fully sufficient.

EXAMPLE B

If very dilute solutions are present, it can be of advantage simply to dip the plate having a concentrating zone into the dilute solution. For this purpose, there is used a plate obtained according to Example 3. The maximum height of immersion is not to exceed the height of the concentrating zone. The actual development begins after the drying of the applied solution. On the edge of the silica gel layer there is first formed a narrow band from which then begins the actual chromatography.

A better application in lines could not be achieved with an automatic application device. Using an equally highly diluted solution, several application in lines, in each case with intermediate drying, would be required applications order to provide the same amount of substance for chromatographic development.

EXAMPLE C

Even in the case of very dilute solutions, due to the concentration on the boundary line to the chromatography layer, detection of the separated substances is still possible. Thus, e.g., on a plate obtained according to Example 1, there were applied from left to right 2, 6, 10, 14 and 18 μl of a 0.001% solution of lipophilic dyestuffs, corresponding to 0.02, 0.06, 0.10, 0.14 and 0.18 μg. After development had taken place, even 20 ng were still detectable on the extreme lefthand path.

EXAMPLE D

The new materials are also outstandingly suitable for the separation of lipophilic dyestuffs which are present in greatly differing concentrations. Onto a coated Alu foil produced according to Example 2 is applied the following:

Test mixture I: 0.005% of a blue dyestuff with higher Rf value 0.5% of a red dyestuff with a lower Rf value Test mixture II: 0.5% of the blue dyestuff with higher Rf value 0.005% of the red dyestuff with lower Rf value Amounts applied were 2, 4, 8 and 16 μl (corresponding to 0.1/10, 0.2/20, 0.4/40 and 0.8 μg/89 μg or vice versa).

The development took place in a standard chamber, without chamber saturation, using toluene up to a running height of 10 cm in the silica gel layer.

After the development, it is shown that in the case of separation of substances with closely adjacent Rf values, small amounts of substances with higher Rf values are easier to separate than small amounts of substances with lower Rf values. The particularly better quality of separation on the foils with concentrating zones is clearly demonstrable.

EXAMPLE E

The advantageous properties can also be well recognized in the case of the separation of amino acids. On a plate obtained according to Example 1 there is applied a mixture of amino acids, the sequence being according to decreasing Rf values:

| L-leucine | DL-threonine |
|---|---|
| DL-valine | glycine |
| α-aminobutyric acid | glutamine |
| α-alanine | arginine |

Amounts applied were 0.75; 2; 4; 6; 8μl of a 0.02% solution of each amino acid, corresponding to 0.15; 0.4; 0.8; 1.2; 1.6μg, respectively.

Development was without chamber saturation in a standard chamber. The elution agent was n-propanol/water (80/20).

The running stretch of the elution agent in the silica gel layer was 10 cm. Detection was by spraying with ninhydrin, (3 minutes heating to 120°0 C.). In comparison with a normal TLC finished plate with silica gel, the separation on the TLC finished plate silica gel having a concentration zone was especially markedly more favorable in the lower Rf range.

EXAMPLE F

In comparison with commercially available plates having a concentrating zone of kieselguhr, the materials according to this invention display a marked superiority. There were compared:

A: A TLC plate silica gel/diatomaceous earth
B: A TLC finished plate silica gel/kieselguhr
C: a plate according to Example 1

As dyestuff solution, there was applied Ceres violet BRN pure, Ceres green BB and blue 18.90 Sandoz, in each case as a 0.1% solution (w/v) in benzene.

(a) The diameters of the applied circular area in the case of several punctate application with a 2 μl capillary on the concentrating zones in question were:

| Amount applied in μl | A | B Diameter in mm | C |
|---|---|---|---|
| 4 | 9 | 10 | 11.5 |
| 8 | 12.5 | 13.5 | 15 |
| 12 | 14.5 | 16 | 18 |
| 16 | 15.5 | 19 | 20.5 |
| 20 | 16 | 21 | 22.5 |
| Average value of the ratio of diameters: (A, B or C/C × 100 | 78 | 90 | 100 |

(b) The diameters of the applied circular areas in the case of punctate application in one run without intermediate drying with a 5 μl and a 20 μl syringe on the concentrating zones in question were:

| Amount applied in μl | A | B Diameter in mm | C |
|---|---|---|---|
| 5 | 10 | 11.5 | 12.5 |
| 10 | 13 | 15 | 17 |
| 20 | 18 | 22 | 25 |
| Average value of the ratio of diameter: (A, B or C/C) X 100 | 76 | 89 | 100 |

The figures show that the commercially available plate B has, on the average, a spreading effect about 10% lower than plate C and plate A one which is about 23% lower, which is brought about by the lower inertness of the concentrating zones in A and B. The greater the diameter of the applied circular area is, the more favorable is the chromatographic separation capacity of the plate for the same quality of the chromatography layer.

EXAMPLE G

The plates or foils having concentrating zones can be employed especially advantageously also in the case of the investigation of biological fluids. The extraction process (clean-up) which is usually necessary for normal chromatography, and which causes losses and/or inexactness, can hereby frequently be omitted. Thus, e.g., direct investigations of body fluids, for example of urine, are possible.

A TLC finished plate produced analogously to Example 3, the silica gel of the chromatography layer of which corresponds to the characteristics described in published German Patent Application No. 25 24 065, is used in the format of 100×100 mm, the concentrating zone of which is 25×100 mm. The layer thickness of the chromatography layer is 200 μm and that of the concentrating zone about 150 μm. The concentrating zone is immersed in rat urine, which contains free biphenyl metabolites to a depth of about 15 mm. Immediately thereafter, the layer is dried by warming. On two places of the concentrating zone there are then applied 2μl amounts of a mixture of biphenylol-(22), biphenylol-(4), biphenyldiol-(2,2') and biphenyldiol-(4,4'), each in 0.01% solution; these applied amounts are then dried. Development takes place in a standard chamber, without chamber saturation, with the elution agent mixture toluene/chloroform/methanol (70/15/15) up to a height of 50 mm in the silica gel layer. After drying, the four metabolite bands in the urine can be recognized in the exact position of the comparison substances in UV or after spraying with potassium hexacyanoferrate (III)-/iron chloride (hRf values biphenylol-(2) about 65, biphenylol-(4) about 50, biphenyldiol-(2,2') about 40 and biphenyldiol-(4,4') about 20–25).

Preparation of the silicon dioxide:

EXAMPLE I 95 g of the following, commercially available $SiO_2$

| particle size | 10–50μm |
|---|---|
| pore volume | 0.72 ml/g |
| specific surface | 580 m²/g |
| average pore width | 60 A | are mixed with 100 ml of an aqueous sodium chloride solution containing 25 g NaCl. The pores are filled with the salt solution upon drying for 12 hours in a drying chamber at 150° C., the product is calcined for 5 hours at 1300° C. The cooled product is washed until free of chloride ions and dried at 150° C. The product obtained has the following characteristica:

| pore volume | 0,19 ml/g |
|---|---|
| specific surface (BET) | 1 m²/g |
| average pore width | 3,5 μm |

EXAMPLE II 150 g of the following silicon dioxide

| pore volume | 0.72 ml/g |
|---|---|
| specific surface | 580 m²/g |
| average pore width | 60 A |
| particle size | 10–50μm | are mixed with 165 ml of an aqueous sodium sulfate solution containing 50 g $Na_2SO_4$. The gel produced is dried in a drying chamber at 150° C.

The silica gel is then calcined for 5 hours at 1100° C. and is washed free of sulfate ions. The silicon dioxide obtained has a pore volume of 0,2 ml/g and a pore width of 3 to 5 μm.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. In a coated substrate for thin layer chromatography which has a concentrating zone layer located in side by side contact with and before the chromatography layer, the improvement wherein the concentrating zone layer consists essentially of porous silicon dioxide having a pore volume of 0.5 ml/g–1.5 ml/g and a pore width of 2–15 $\mu$m.

2. The coated substrate of claim 1, wherein the silicon dioxide of the concentrating zone has a particle size distributed in the range of 10–50 $\mu$m.

3. The coated substrate of claim 1, wherein the layer thickness of the concentrating zone is 100–200 $\mu$m.

4. The coated substrate of claim 3, wherein the layer thickness of the chromatography layer is 200–300$\mu$m.

5. The coated substrate of claim 1, wherein the specific surface area of the silicon dioxide in the concentrating zone is less than 1 $m^2/g$.

6. The coated substrate of claim 1, wherein the pore width is 4–8 $\mu$m.

7. The coated substrate of claim 1, wherein the chromatography layer consists essentially of chromatographically active silica gel.

8. The coated substrate of claim 1, wherein the layers contain 0.1 to 10 wt.% of binding agents and 0.5 to 5 wt.% of indicator, the wt.% being based on the composition of the layer in finished form.

9. The coated substrate of claim 1, wherein the silicon dioxide of the concentrating zone is synthetically produced and has a pore volume of 0.5–1.0 ml/g, a pore width of 4–8 $\mu$m, a particle size in the range of 10–50 $\mu$m and a specific surface area of 0.2–0.8 $m^2/g$; the thickness of the concentrating zone layer is 100–200 $\mu$m and of the chromatography layer is 200–300 $\mu$m; and the chromatography layer consists essentially of a chromatographically active silica gel.

10. A method of separating components of a test sample which comprises placing the test sample in the concentrating zone of the coated substrate of claim 1 and subsequently placing eluent into the concentrating zone so that the test sample flows from the concentrating zone into the chromatography layer.

* * * * *